United States Patent [19]

Bentley

[11] Patent Number: 5,238,925
[45] Date of Patent: Aug. 24, 1993

[54] ANGIOGENIC FACTOR ISOLATED FROM LIVE YEAST CELL DERIVATIVES AND ITS USE IN TREATING WOUNDS OR BURNS IN MAMMALS

[75] Inventor: J. Peter Bentley, Portland, Oreg.

[73] Assignee: The State of Oregon Acting by and through The State Board of Higher Education on Behalf of the Oregon Health Sciences University, Portland, Oreg.

[21] Appl. No.: 521,149

[22] Filed: May 9, 1990

[51] Int. Cl.$^5$ .................. A61K 37/02; C07K 3/02; C07K 15/00

[52] U.S. Cl. .................. 514/21; 514/2; 514/925; 530/323; 530/338; 530/824; 530/416; 530/417; 530/412; 530/300; 530/371

[58] Field of Search .................. 514/12, 21, 925; 530/300, 371, 323, 338, 824, 416, 417, 412

[56] References Cited

U.S. PATENT DOCUMENTS

| | | | |
|---|---|---|---|
| 2,239,345 | 4/1941 | Sperti | 424/553 |
| 2,320,478 | 6/1943 | Sperti | 424/195.1 |
| 4,284,552 | 8/1981 | Bucovaz | 530/371 |
| 4,575,457 | 3/1986 | Mazarin | 424/52 |
| 4,707,542 | 11/1987 | Friedman | 530/395 |
| 4,942,031 | 7/1990 | Levin | 514/178 |

OTHER PUBLICATIONS

Goodson et al., J. Surge. Res. 21:125–129, 1976.
Subramanyam et al., Digestive Diseases and Sciences 29:829–832, 1984.
Kaplan, Arch. Surge. 119:1005–1008, 1984.
Hunt et al., Inflammation and wound Healing, 96:48–54, 1984.
Banda et al., Proc. Natl. Acad. Sci. USA, 79:7773–7777, 1982.
Vu et al., Laboratory Investigation, 53:499–508, 1985.
Dusseau et al., Circ. Res., 59:163–170, 1986.
Bentley et al. Arch. Surge. 125:641–648, 1990.

*Primary Examiner*—F. T. Moezie
*Attorney, Agent, or Firm*—Darby & Darby

[57] ABSTRACT

Disclosed herein is purified isolated angiogenic factor, isolated from Live Yeast Cell Derivative. Also disclosed herein are methods to treat mammals suffering from wounds or burns comprising administering the angiogenic factor and pharmaceutical formulations for use in the methods.

6 Claims, 5 Drawing Sheets

ANGIOGENIC FACTOR ISOLATED FROM LIVE YEAST CELL DERIVATIVES AND ITS USE IN TREATING WOUNDS OR BURNS IN MAMMALS

BACKGROUND OF THE INVENTION

The present invention is directed to an angiogenic factor, pharmaceutical formulations comprising effective amounts of the angiogenic factor and methods of use thereof as a wound healing agent.

The course of wound healing can be influenced pharmacologically. Dietary compounds, such as vitamins A and C, zinc, protein, as well as oxygen, can have a direct influence on the course of wound healing. Addition of any one of these compounds to a wound otherwise deprived of that compound will augment aspects of the healing of that wound.

Growth factors are believed to promote wound healing. For example, epidermal growth factor (EGF) present in saliva is believed to accelerate wound healing in mice. Schultz, G. S. et al. (Science 232:350–352, 1986) reported that transforming growth factor (TGF)-alpha and vaccinia virus growth factor (VGF), both of which are substantially homologous to EGF, accelerated epidermal wound healing in pigs when topically applied to second degree burns and were significantly more active than EGF.

Also known are a variety of angiogenic (literally "blood-vessel-forming") growth factors, such as fibroblast growth factors (FGFs) which are believed to promote growth and organization of endothelial cells (which line blood vessels) into new blood vessels. Preliminary evidence indicates that the two known (sequenced) angiogenic growth factors, basic and acidic FGF (so named due to the total net charge on the molecules) may be of use as wound healing agents.

Angiogenesis is an essential part of wound healing. Angiogenesis can be described as the directed outgrowth of new capillaries towards a specific stimulus. Under microscopic evaluation, endothelial cells (cells which line blood vessels) can be seen to migrate from the tip of the capillary before any induction of mitosis (or cell division).

Skin Respiratory Factor (SRF) is an aqueous alcoholic extract of Brewer's Yeast (*Saccharomyces cervisiae*). SRF has been employed as a wound healing agent and is an ingredient in a proprietary hemorrhoidal medication (Preparation H ®).

Goodson, W. et al. (*J. Sur. Res.* 21:125–129, 1976) disclosed the augmentation of some aspects of wound healing by SRF. SRF increased the in vitro synthesis of collagen by human skin homogenates, the consumption of oxygen by cultured fibroblasts, and augmented epithelialization of moist open wounds in rabbits.

Subramanyan, K., et al. (*Dig. Dis. Sci.* 29: 829–832, 1984) disclosed a beneficial effect of a pharmaceutical preparation containing SRF upon the healing of artificially induced ulcers.

Kaplan, J. Z. (*Arch. Suro.* 119: 1005–1008, 1984) conducted a double blind randomized study of 26 human skin graft donor sites. Kaplan reported that earlier angiogenesis and epithelialization occurred in those sites treated with an ointment containing the above-mentioned yeast factor compared with donor sites in the same patients which were treated with a control ointment. Kaplan referred to the material he used as "Live Yeast Cell Derivative" (LYCD). LYCD was prepared in the exact same manner as SRF.

Mazarin, U.S. Pat. No. 4,575,457 issued Mar. 11, 1986, disclosed pharmaceutical compositions comprising SRF which were said to provide effective therapy for gingivitis when brushed on the teeth and gingivae.

The SRF employed in the above-mentioned publications was the crude alcohol-extracted material obtained from live yeast cell derivatives (LYCD). SRF is a dark brown viscous fluid and it is not known which of its many components are responsible for the various biological activities contained therein. No one has previously fractionated this material in order to identify the active (or any) factors present therein. There is a need in the art for improved wound healing compositions which can be used to treat mammals suffering from wounds such as hemorrhoids, decubitus ulcers (bed sores), other wounds or burns. As SRF has been used safely and effectively in a proprietary over the counter wound healing medication for over forty-five years, its use in a purified form would be expected to be highly efficacious.

Therefore, it is an object of the present invention to identify the active wound healing principle(s) in SRF.

It is another object of the present invention to fractionate and purify said active principle(s).

A further object of the present invention is to provide pharmaceutical formulations for treating mammals suffering from wounds or burns.

These and other objects of the present invention will be apparent to those of ordinary skill in the art in light of the present description, claims and drawings.

SUMMARY OF THE INVENTION

The present inventor has identified and isolated the active wound healing principles present in LYCD. These have been found to be angiogenic peptides which can be conveniently and rapidly isolated.

In one aspect, the present invention provides a purified isolated angiogenic factor comprising a mixture of polypeptides having molecular weights ranging between about 6,000 daltons and about 17,000 daltons, said factor isolated from a live yeast cell derivative.

In another aspect, the present invention provides a method for treating mammals suffering from wounds or burns comprising administering to mammals in need of such treatment an effective amount of a purified isolated angiogenic factor comprising a mixture of polypeptides having molecular weights ranging between about 6,000 daltons and about 17,000 daltons, said factor isolated from a live yeast cell derivative and a pharmaceutically acceptable carrier or diluent.

In a further aspect, the present invention provides a pharmaceutical formulation for treating wounds or burns in mammals comprising an effective amount of a purified isolated angiogenic factor comprising a mixture of polypeptides having molecular weights ranging between about 6,000 daltons and about 17,000 daltons, said factor isolated from a live yeast cell derivative.

DETAILED DESCRIPTION OF THE INVENTION

All patents and literature references cited in this specification are hereby incorporated by reference in their entirety.

In the specification, the following terms are defined as follows:

"LYCD" is defined as an alcoholic extract obtained from yeast prepared as described below and will be used interchangeably with "SRF".

The "angiogenic factor of the present invention" is defined as the biologically-active polypeptide fraction obtained from LYCD.

The present inventor has isolated an angiogenic factor from live yeast cell derivative (LYCD) for use as a wound healing agent. This factor has been found to be comprised of four polypeptide fractions ranging in molecular weights between about 6,000 daltons and about 17,000 daltons. The angiogenic factor of the present invention has been characterized by its positive reactivity with ninhydrin, amino acid compositions of each of the four polypeptide fractions and its behavior on anion exchange and molecular sieve chromatography columns. When used in assays specific for angiogenesis and/or wound healing it has been found to be extremely active.

The present inventor has also devised an isolation scheme suitable for the large scale preparation of the angiogenic factor obtainable from crude LYCD using anion exchange chromatography and/or molecular sieve chromatography. An example of a large scale batch purification of LYCD using anion exchange chromatography is shown in Example 4 below.

The isolated angiogenic factor of the present invention has been found to be active at concentrations 25-fold lower than the unfractionated LYCD in a chick embryo yolk sac angiogenesis assay. In addition, it was also active in a rabbit cornea assay which measures new blood vessel formation and it stimulated wound healing in the "Schilling/Hunt" wire mesh cylinder model as shown in Example 5 below. These assays are recognized by those skilled in the art as good indicators of wound healing activity.

The present inventor has found that the major component present in LYCD is an inert carbohydrate, probably trehalose. This can be advantageously removed by any one of a variety of different techniques such as dialysis, ultrafiltration and preferably anion exchange chromatography.

From the experiments described below in Examples 1-5, it has been found that the wound healing effects of LYCD are due to a mixture of peptides and/or small proteins with molecular weights ranging between about 6,000 daltons and about 17,000 daltons. These peptide fractions can be isolated by use of gel filtration (molecular sieve chromatography) or other procedures which separate molecules on the basis of size such as dialysis. An alternative isolation procedure involves removal of the large amount the inert carbohydrate by use of anion exchange resins or dialysis prior to isolation of the peptides by molecular sieve chromatography.

The angiogenic factor of the present invention has been isolated from LYCD prepared from Saccharomyces cervisiae (Brewer's yeast). Other yeast strains, such as Saccharomyces diastaticus, or Saccharomyces steineri could also be used to obtain the LYCD using the techniques described below in Example 1. Saccharomyces cervisiae is preferred because of its commercial availability being of primary use to the baking industry. These yeast strains are available from numerous commercial sources, such as Gist-Brocades Food Ingredients (Willow Grove, Pa.) and Universal Foods Corporation (East Brunswick, N.J.).

In an alternitive embodiment of the present invention, dialysis (using membranes which will retain greater than 6000 molecular weight components) against a physiologically acceptable buffer, such as phosphate buffered saline (PBS) at between about 4° C. and 20° C. for between about 12 and about 48 hours of diluted LYCD can be employed to remove low molecular weight compounds and concentrate the higher molecular weight compounds, including the angiogenetic peptides of the present invention. Such dialysis membranes are commercially available from numerous commercial sources such as SPECTRA-POR ® (Spectrum Medical Industries Inc., Los Angeles, Calif.). The angiogenic peptides can used at this point or further purified by molecular sieve chromatography as detailed below.

The angiogenic factor of the present invention may be isolated from the crude LYCD by any protein purification techniques which separate components on the basis of charge and/or size, preferably anion exchange chromatography and/or molecular sieve chromatography. Anion exchange chromatography of the crude LYCD followed by molecular sieve chromatography is a particularly preferred isolation sequence.

Ammonium sulfate precipitation of the peptides followed by High Performance Liquid Chromatography (HPLC) using reverse phase or sizing columns may alternatively be employed to isolate the angiogenic peptides of the present invention.

An example of anion exchange chromatography using such is detailed in Example 2 below and comprises binding the angiogenic factor of the present invention present in crude LYCD to an anion exchange residue medium, washing the medium with a non-charged solvent, discarding the wash, eluting the factor from the medium with between about 0.1 to 1M acid and recovering the factor from the acid eluate. Non-limiting examples of suitable non-charged solvents for use with the anion exchange media in the present invention include deionized water and preferably distilled water. Non-limiting examples of suitable acids for use in the present invention, include but are not limited to HCl, or weak acids and preferably acetic acid between the concentration range of about 0.1 and about 1M and preferably between 0.4 and about to 1M.

Anionic exchange media suitable for use in the present invention include but are not limited to Amberlite (Rohm and Haas Company, Philadelphia, Pa.), AG 1-X2 (Bio-Rad, Richmond, Calif.), and preferably Dowex-1 (Dow Chemical Company, Midland, Mich.).

The angiogenic factor of the present invention at this stage can be used as a wound healing agent or, alternatively can be further purified by molecular sieve chromatography as shown in Example 4 below. The molecular sieve column results in an additional 25-fold purification.

An example of a molecular sieve chromatographic isolation of the angiogenic factor of the present invention is shown in Example 2 below. Using this technique, the LYCD is loaded onto a suitable molecular sieve column (such as Sephadex-G50 or Sephadex-G25), the excluded fraction, and fractions of included material are collected and assayed for angiogenic and/or wound healing activity. The active fractions are identified and pooled or maintained separately, depending on the desired use.

Molecular sieve media suitable for use in the present invention are those which separate proteins having molecular weights of the polypeptide fractions of the present invention, i.e., ranging between about 6,000 daltons and about 17,000 daltons These include but are not limited to Bio-Gel P6 and Bio-Gel P10 (Bio-Rad, Richmond, Calif.) and preferably Sephadex G-25 and Sephadex G-50 (Pharmacia Fine Chemicals, Piscataway, N.J.).

The purification procedure is rapid, relatively inexpensive and can be performed in a column format or, preferably as a batch process. Moreover, the yield of the angiogenic factor of the present invention is very high. For all of the above reasons, these procedures are well suited for large scale (and small scale) preparation of the angiogenic factor of the present invention.

The angiogenic factor of the present invention can be used as a wound or burn healing agent in the form of a mixture of the angiogenic peptides obtainable from anion exchange chromatography as shown in Example 4 below or in any combination of the four individual peptide fractions which result from fractionation of LYCD by molecular sieve chromatography as shown in Example 2 below.

Once obtained, the angiogenic factor of the present invention can be employed in a method for treating mammals suffering from wounds (such as decubitus ulcers or hemorrhoids) or burns comprising administering to a mammal in need of such treatment an effective amount of the angiogenic factor of the present invention and a pharmaceutically acceptable carrier or diluent. The effective amounts of the angiogenic factor of the present invention can be determined by routine experimentation well-known in the art, e.g. by establishing a matrix of dosage and frequency and assigning a group of experimental subjects to each point of the matrix, as well-known in the art. Design of this experiment should preferably also take into account the tissue accumulation properties of the angiogenic factor of the present invention.

When employed as a wound or burn healing agent, the angiogenic factor of the present invention may be administered to a mammal in need of such treatment in dosage forms orally, parenterally, or preferably, topically directly to the affected area in effective amounts. The number of treatments and the duration of treatments may vary from individual to individual depending upon the severity of the wound or burn.

The angiogenic factor of the present invention may be prepared in pharmaceutical formulations or dosage forms to be used as a wound or burn healing agent. It will be appreciated that the unit content of active ingredients contained in an individual dose of each dosage form need not in itself constitute an effective amount since the necessary effective amount can be reached by administration of a plurality of topical dosage forms, capsules, tablets, injectables or combinations thereof.

Pharmaceutical formulations of solid dosage forms such as tablets, capsules, cachets, pills, bulk or unit dose powders and granules, of topical dosage forms such as solutions, powders, fluid emulsions, fluid suspensions, semisolids, ointments, pastes, creams, gels or jellies, and rigid foams, and of parenteral dosage forms such as solutions, suspensions, emulsions, or dry powder, comprising effective amounts of the angiogenic factor of the present invention (or physiologically acceptable salts thereof) as at least one of the active ingredients would in addition contain pharmaceutically acceptable diluents or fillers, disintegrants, binders, lubricants, surfactants, hydrophobic vehicle, water-soluble vehicles, structural matrix formers, suspending or viscosity-inducing agents, emulsifiers, buffers, humectants, skin protectants, moisturizers, solubilizers, and preservatives. Numerous pharmaceutically acceptable and compatible optional materials can be found in various pharmacological references. Two such references are "Modern Pharmaceutics", G. S. Banker and C. T. Rhodes, Marcel Dekker, Inc., 1979 and "The Theory and Practice of Industrial Pharmacy", L. Lachman, H. A. Lieberman, and J. L. Kanig, Lea & Febiger, 1970.

Exemplary materials of the above components include lactose and dicalcium phospate as diluents; starch and sodium starch glycolate as disintegrants; microcrystalline cellulose and polyvinylprolidone as binders; stearic acid and magnesium stearate as lubricants; sodium lauryl sulfate as a surfacetant; mineral oil and petrolatum as hydrophobic vehicles; propylene glycol and glycerol as water-soluable vehicles; stearyl alcohol as structural matrix former; veegum as a viscosity-inducing agent; Tweens and Arlacels as emulsifiers; acetates, citrates, and phosphates as buffers; polyethylene glycol and gelatin as hydrolysates and cellulose gums as moisturizers; polyethylene glycol as a solubilizer; and parabens and benzalkonium chloride as preservatives.

The present invention is described further below in specific examples which are intended to illustrate the present invention without limiting its scope.

EXAMPLE 1

Preparation of LYCD

LYCD is an alcoholic extract from yeast (*Saccharomyces cervisiae*) produced by the methods set forth in U.S. Pat. Nos. 2,239,345, 2,320,478, and 2,320,479

Briefly, 960 gm of fresh live Brewer's yeast (*Saccharomyces cervisiae*, Universal Food Corporation) was added to a jacketed reaction vessel (Aldrich Chemical Co., Inc., Milwaukee, Wis.) containing 1 liter of methanol-denatured ethanol. The mixture was gently agitated for 2 hours at 60° C. while stirring, the hot slurry was cooled to 50° C. and 67 gm of celite was added. The mixture was then cooled to 35° C. and vacuum filtered. The filtrate was treated with 5.9 gm of charcoal, stirred for 1 hour at ambient temperature and filtered as above. The alcohol was removed under vacuum and the filtrate was further concentrated on a Rotavap to yield 57 ml of aqueous solution.

The LYCD concentrate was a viscous brown syrup with a specific gravity of 1.26 and a total solids content of 51.5%. It was diluted with two volumes of distilled water and clarified by centrifugation for one hour at 43,000 $\times$ g. A small pellet (92 mg), consisting of cellular debris, was obtained from 100 ml of LYCD and discarded. The clarified supernatant fraction was used for all subsequent experiments.

EXAMPLE 2

Molecular Sieve Chromatography LYCD

The LYCD used in the experiments reported below were analyzed in terms of its carbohydrate content using the Orcinol procedure (Lee, W. C. et al. *Anal. Biochem.* 43:640–643, 1971) and for protein content using Ninhydrin reactivity (Research Bulletin No. 20, Technicon Corporation, Ardsley, N.Y., 1968).

Analysis of the crude starting material showed 38.5% of the dry weight of the LYCD was carbohydrate (expressed as glucose equivalents) using the Orcinol procedure and 41.2% of the dry weight was protein (expressed as leucine equivalents) as calculated by its reaction with Ninhydrin. The latter figure increased slightly to 48.3% after hydrolysis (for 18 hours in 6N HCl). Thus, by far the largest proportion of LYCD was accounted for as Orcinol reactive carbohydrate and free amino acids together with a small amount of protein or peptide material.

A sample of clarified LYCD was applied to a column of Sephadex G-25 (Pharmacia Fine Chemicals, Piscataway, N.J.). Three mls of clarified LYCD diluted to 15 mls with distilled water was applied to a 2.5×72 cm column and eluted with distilled water at a rate of 20.4 mls/hr. The results are shown in FIG. 1.

Figure 1A:
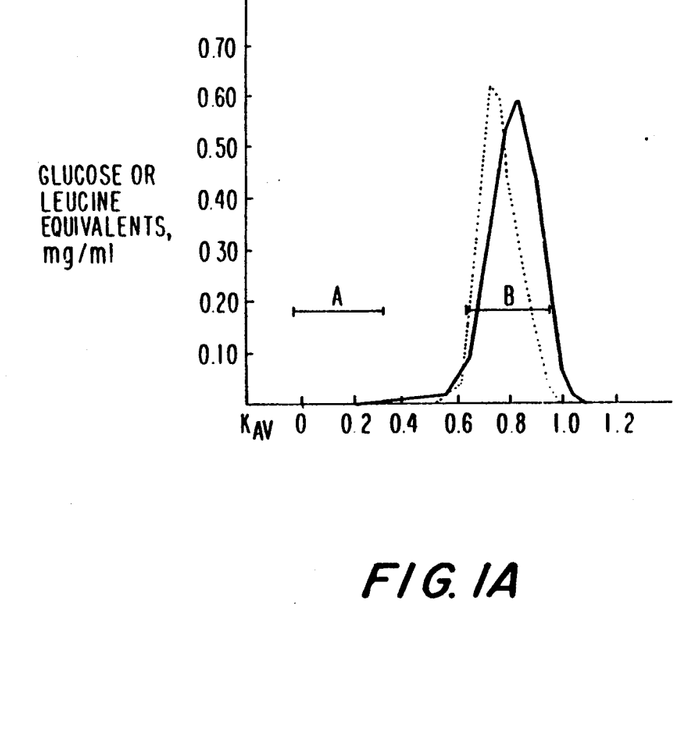
FIG. 1A is a graph of the elution profile of LYCD fractionated on Sephadex G-25 superfine.
Figure 1B:
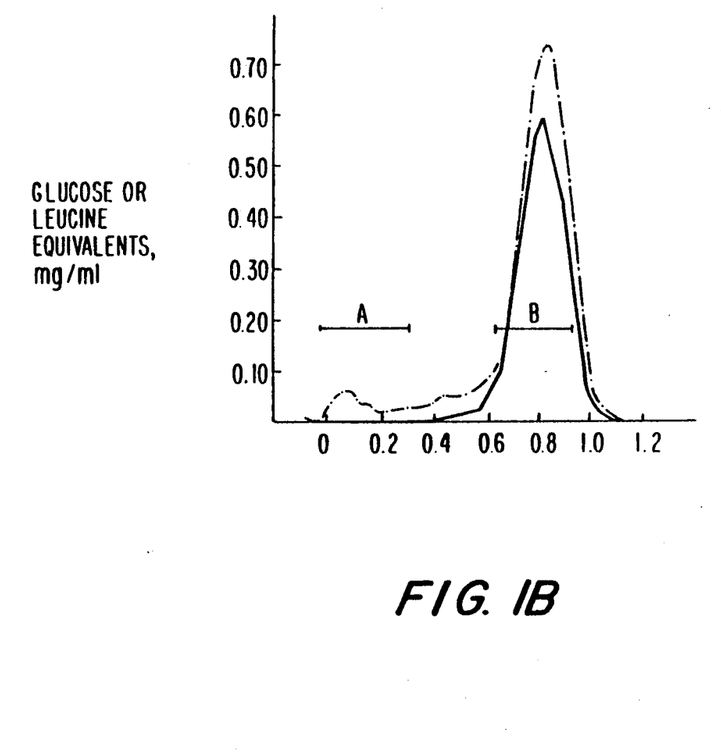
FIG. 1B is a graph of the fractionation of LYCD on Sephadex G-25 superfine before and after hydrolysis.

In FIG. 1 dotted lines represent Orcinol reactivity expressed as glucose equivalents and solid lines represent Ninhydrin reactivity expressed as leucine equivalents. Two broad fractions were collected, pooled and lyophilized for further study. Fraction A, which eluted at the exclusion volume of the column (greater than 25,000 daltons molecular weight) had a brown color and displayed little Ninhydrin reactivity (FIG. 1A). After hydrolysis, a distinct peak of Ninhydrin reactivity was seen (FIG. 1B) indicating the presence of protein or peptides in this fraction. On a weight basis, fraction A represented 1.7% of the dry weight material applied to the column. Fraction B was quantitatively the major fraction, with 84% of the applied materials being recovered in this fraction. Nearly all of the Ninhydrin reactivity and all of the Orcinol reactivity was located under this peak. A small amount of a yellow colored material was seen to interact with the Sephadex and was eluted after the total volume of the column (as determined by a separate column run with tritiated water). Essentially the same pattern as shown in FIG. 1 was obtained when another column treated the same way was eluted with 0.1M NaCl. Water elution was therefore chosen for all subsequent column runs in order to simplify preparation of the low molecular weight samples for the bioassays which can be effected by the presence of salts.

Figure 2:
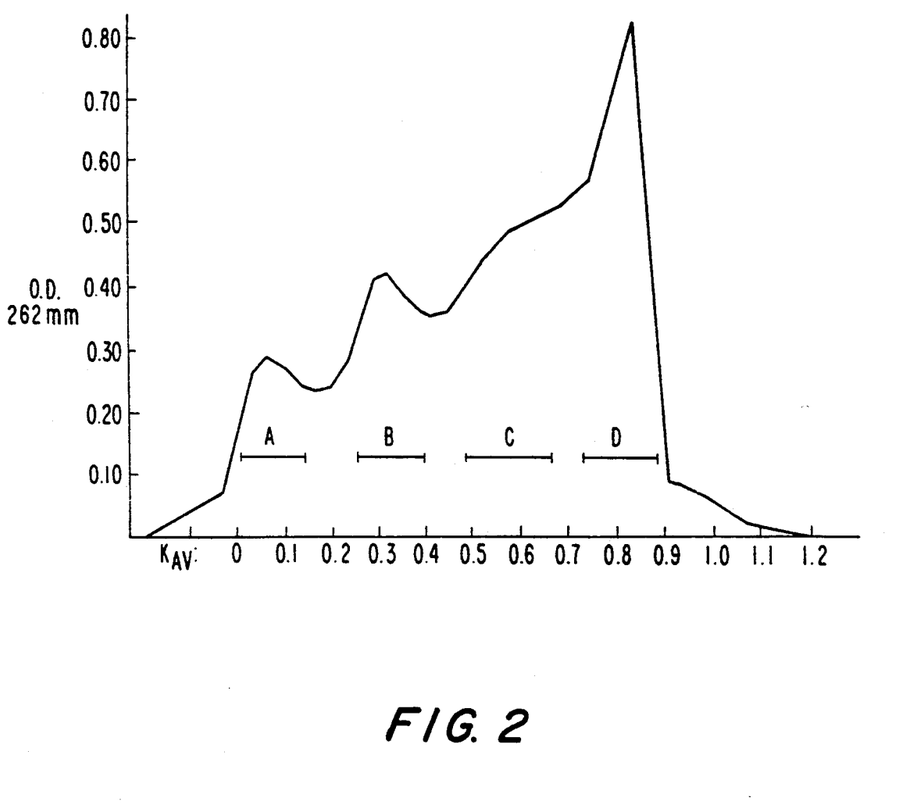
FIG. 2 is a graph of the elution profile of fraction A from FIG. 1A on Sephadex G-50 superfine.

A sample of fraction A from FIG. 1 was applied to a column of Sephadex-G50 (Pharmacia Fine Chemicals) under conditions described above. This resulted in a further subfractionation as shown in FIG. 2, although discrete peaks were not obtained. On the basis of the published fractionation range for Sephadex-G50, it was estimated that fraction A was a mixture of materials with molecular weights ranging between about 30,000 daltons to below 1,500 daltons.

In FIG. 2 an aliquot of fraction A derived from 1 ml of LYCD was applied to a 1.5×63 cm Sephadex-G50 column and was eluted with distilled water at a rate of 8.7 mls/hr. Fractions A-D were collected as indicated in FIG. 2 and lyophilized for further study.

It was clear from the elution profile shown in FIG. 2 that each fraction was probably a mixture of more than one peptide. This was borne out by the results of polyacrylamide gel electrophoresis as shown in FIG. 3.

Figure 3:
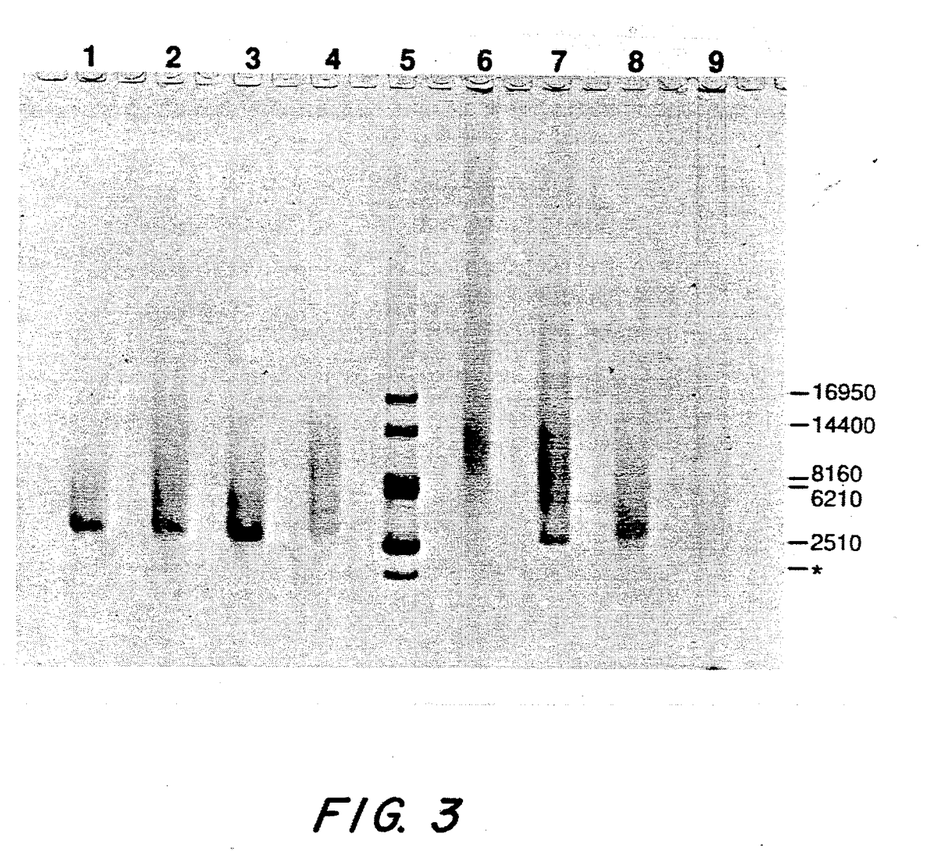
FIG. 3 is a gel showing the electrophoresis of the LYCD peptide fraction in a 16% polyacrylamide gel.

In FIG. 3, each of the four fractions isolated from the Sephadex-G50 column were electrophoresed in a 16% polyacrylamide gel (Laemmli, U. K., *Nature* 227:680–685, 1970). In FIG. 3 lanes 1 and 2 are the peptides (fraction A, FIG. 1) from two different batches of LYCD; lane 3 is the peptide fraction from FIG. 1, further purified by chromatography on an anion exchange (Dowex-1, Dow Chemical Co., Midland, Mich.) as shown below in FIG. 5; lane 4 is the peptide fraction isolated by gel filtration of fraction B, FIG. 5; lane 5 are molecular weight markers; lane 6 is fraction A, FIG. 2; lane 7 is fraction B, FIG. 2; lane 8 is fraction C, FIG. 2; and lane 9 is fraction D, FIG. 2. It should be noted that the bottom band in the molecular weight markers (indicated by a star in FIG. 3) is an artifact present in these markers as shipped by the manufacturer (Sigma Chemical Co., St. Louis, Mo.).

On the basis of polyacrylamide gel electrophoresis, the molecular weight range of the peptide fraction was estimated to be between about 6,000 daltons and about 17,000 daltons. Each of the peptide fractions applied to the column ran as a broad band in contrast to the known marker peptides which ran as sharp discrete bands. This was true of the high molecular weight material (fraction A from FIG. 1), three of the four subfractions from FIG. 2 and of the high molecular weight component of the peptide fraction isolated from LYCD by ion exchange resin (see below). The four subfractions from the Sephadex-G50 column appeared to be distinct based upon the amino acid analysis as set forth in Table 1 below:

TABLE 1

Amino acid analysis of LYCD fractions

| | Low mol. wt. fraction | Peptide subfractions (FIG. 2)** | | | |
|---|---|---|---|---|---|
| | FIG. 1 Fraction B* | A | B | C | D |
| ASP | 26 | 115 | 132 | 138 | 64 |
| THR | 10 | 102 | 67 | 41 | 21 |
| SER | 10 | 117 | 89 | 76 | 32 |
| GLU | 410 | 135 | 156 | 157 | 249 |
| PRO | 38 | 51 | 43 | 50 | 22 |
| GLY | 26 | 110 | 118 | 128 | 304 |
| ALA | 208 | 137 | 129 | 110 | 47 |
| ½ CYS | 0 | 4 | 3 | 7 | 117 |
| VAL | 19 | 49 | 50 | 50 | 25 |
| MET | 0 | 4 | 10 | 11 | 10 |
| ILE | 7 | 25 | 19 | 20 | 13 |
| LEU | 5 | 31 | 34 | 41 | 30 |
| TYR | 0 | 2 | 1 | 1 | 2 |
| PHE | 0 | 19 | 19 | 18 | 9 |
| HIS | 66 | 11 | 12 | 16 | 8 |
| LYS | 176 | 74 | 100 | 115 | 36 |
| ARG | 0 | 15 | 19 | 20 | 11 |

Results are expressed as Residues/1000 residues.
*Analysis by amino acid analyzer (Beckman, Palo Alto, CA). Total free amino acids in this fraction were 32.7 mg/100 mg fraction prior to hydrolysis and 39.8 mg/100 mg after hydrolysis.
**By HPLC method (Negro, A., et al. *Anal. Biochem.* 160: 39–46, 1987).

As can be seen from the results in Table 1 above, fraction A had no cysteine whereas fraction D was rich in cysteine. A common feature of all the peptide fractions was the relatively high content of negatively charged amino acids which together comprised 12% to 20% of the total peptide, and the positively charged amino acid lysine which was present at about 6% (Table 1).

EXAMPLE 3

Analysis of the Carbohydrate Component of LYCD

The major component of LYCD (fraction B, FIG. 1) was composed of a carbohydrate and of amino acids together with a small amount of low molecular weight peptides based upon the Orcinol and the Ninhydrin reactivities. A specimen of this material was applied to the neutral sugar analyzer column (as described in Lee, y C. et al. suora) both before and after hydrolysis with a 40% suspension of Dowex 50-x2 in 0.01N HCl as described below.

2.5 microliters of pooled fraction B (from FIG. 1) was hydrolyzed in 100 microliters of a 20% w/v suspension of Dowex 50-X2 (H+) in 0.2N HCl for 40 hours at 100° C. and diluted to 2.0 mls with distilled water. Another aliquot was similarly diluted without hydrolysis. 0.5 ml of this was injected into 0.9×20 cm column of an ion exchange resin (DA-X 4, Durrum Chemical Corp., Palo Alto, Calif.). The column was eluted at 1.2 ml/min. with a concave pH gradient in 0.45M borate buffer as described (Lee, W. C., et al. Anal. Biochem. 43:640–643 (1971)). The results are shown in FIG. 4.

Figure 4:
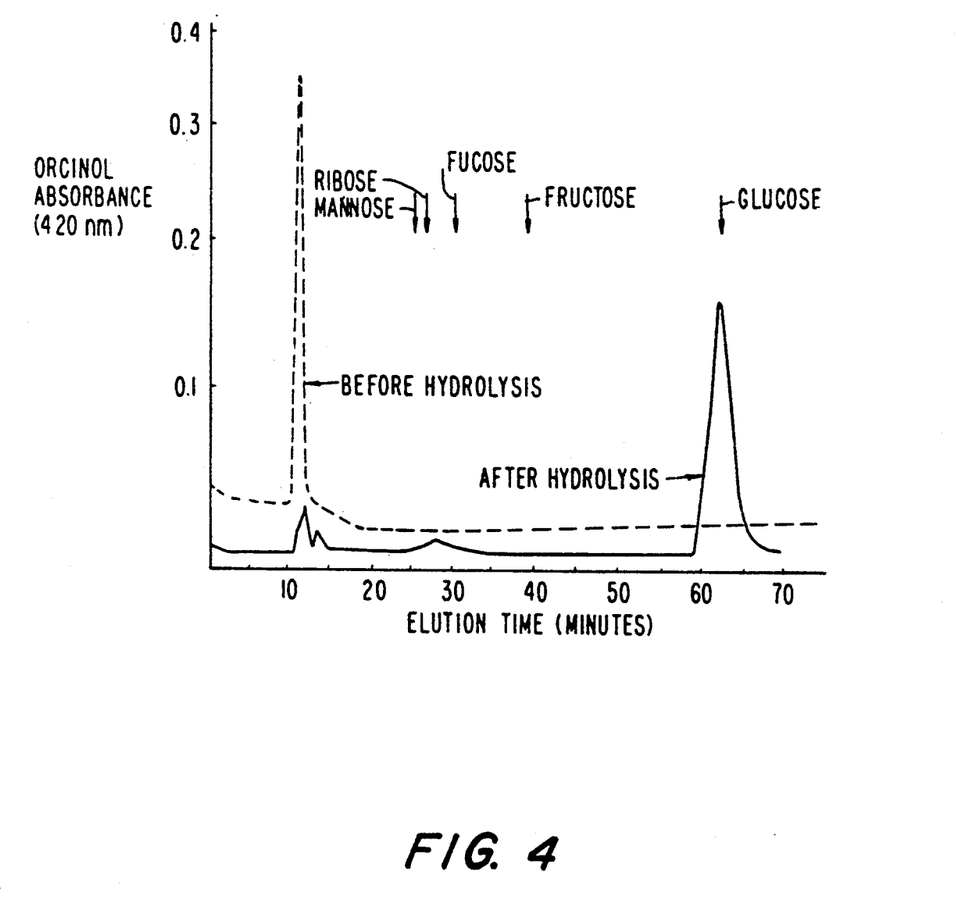
FIG. 4 is a graph showing the chromatography of the carbohydrate component of LYCD on an anion exchange resin.

Before hydrolysis a single sharp peak which did not correspond to any of the marker sugars was eluted (FIG. 4). After hydrolysis this peak was virtually absent and a large peak corresponding to glucose appeared. A further sample of the fraction was eluted from a column of Sephadex-G10 (Pharmacia Fine Chemicals) which had previously been calibrated with specific carbohydrate markers and with $^3H_2O$. All of the applied material eluted as a single sharp peak at the location of a disaccharide. Since glucose was the only known monoaccharide component, the material was digested with alpha-glucosidase which would have been expected to degrade the glucose containing disaccharide maltose. The material was completed resistent to glucosidase and it was concluded that the glucose residues were not linked by an alpha 1–4 bond. The original material exhibited virtually no reducing activity when tested by the ferrocyanide procedure (Park, J. T. and Johnson, M. J., J. Biol. Chem. 181: 169, 1949) which indicated that neither of the number 1 carbons of the glucose residues were free. Therefore, it was concluded that the carbohydrate component of LYCD consisted of a glucose disaccharide in which the glucose molecules were linked by a 1—1 bond. This structure is consistent with trehalose, which is abundant in yeast. The commercial preparation of trehalose involves its extraction from yeast with ethanol as used in the LYCD extraction process.

EXAMPLE 4

Ion Exchange Chromatographic Fractionation of LYCD

The quantitatively major components of LYCD were trehalose and an amino acid component and these co-elute when fractionated on the basis of size (fraction B, FIG. 1). Because the trehalose is uncharged it was possible to remove it by ion exchange chromatography. A variety of resins were tested and good separation was obtained using Dowex-1 in the hydroxyl form as shown in FIG. 5.

Figure 5:
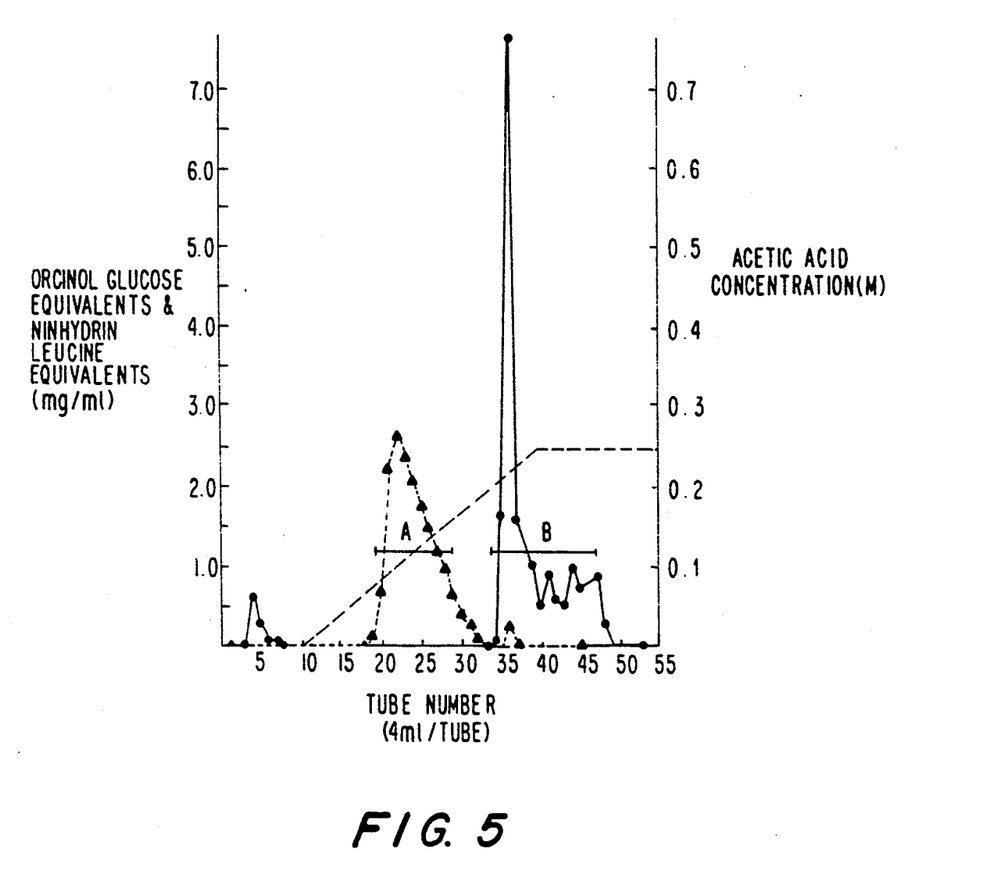
FIG. 5 is a graph showing the fractionation of LYCD on a column of Dowex 1-XB.

In FIG. 5, 0.4 ml of clarified LYCD, diluted to 2 ml was applied to a 1.5×10 cm column of Dowex-1 which had been converted to the hydroxyl form. It was eluted at a rate of 60 ml/hr with (1) 40 mls of distilled water (including the sample), (2) 120 mls of 0–0.5M acetic acid in a linear gradient as shown by the dashed line, and (3) 80 mls of 0.5M acetic acid as shown by the dashed and dotted line. Individual tubes were assayed for Orcinol activity and expressed as glucose equivalents (dotted line) and Ninhydrin reactivity expressed as leucine equivalents (solid line) without prior hydrolysis. The results are shown in FIG. 5.

As can be seen from FIG. 5, water eluted a small amount of Ninhydrin positive material (probably positively charged amino acids or peptides). Elution with a gradient of acetic acid from 0–0.5M eluted nearly all of the carbohydrate in a broad peak between 0.15M and 0.35M acetic acid. The Ninhydrin positive material was eluted as a sharp peak at a concentration of approximately 0.4M acetic acid. Similar results to that shown in FIG. 5 were obtained when samples of either whole LYCD, peak A or peak B from FIG. 1, were fractionated by the Dowex procedure. The peptide fractions from each peak eluted in the same position. It is thus possible to isolate the high molecular weight peptides and amino acid fractions from LYCD by a one step procedure. This column procedure was subsequently modified so that bulk separations could be carried out. 12.5 mls of LYCD diluted to 250 mls was slurried with 150 grams of Dowex 1-X8 and stirred in a Buchner frittered glass funnel for five minutes. The fluid was aspirated and discarded and the resin was slurried with 250 mls of 0.1M acetic acid. The fluid was aspirated and the resin reslurried with 0.1M acetic acid. Upon aspiration of this material, it was found that 93% of the Orcinol reactive material could be removed by two washes with 0.1M acetic acid. Subsequently washing the resin with two aliquots of 250 mls of 1M acetic acid resulted in the recovery of 79.8% of the total Ninhydrin material applied to the column. Subsequent elution with 2×250 mls aliquots of distilled water resulted in recovery of an additional 5.8% of the Ninhydrin positive material.

Based upon the separation scheme described above, the fraction comprising the peptides would be expected to contain proteins or peptides large enough to be excluded from Sephadex-G25 and smaller peptides or free amino acids which would elute at roughly the same position as a disaccharide. When this mixed fraction was reapplied to a Sephadex-G25 column and eluted with water as described above the results were virtually identical to those seen in FIG. 1B. Thus, the peak observed at the exclusion volume of the column had little Ninhydrin reactivity unless it was hydrolyzed as above. A second much larger peak was seen as in FIG. 1B and this peak consisted of free amino acid residues (see Table 1).

EXAMPLE 5

Bioaasays

1. Chick Embryo Angiogenesis Assay

Samples obtained from the different fractionation procedures described above were screened for biological activity using the chick embryo angiogenesis assay. This procedure, which is relatively rapid, not only indicated the fraction in which major biological activity resides but also provided dose/response information for use in the next level of biological testing.

The embryos were cultured as described by Auerbach et al. (J. Develop. Biol. 41:391, 1974) and Taylor and Weiss (*Int. J. Microcirculation* 3:337, 1984). The assay is based upon the observation of neovascularization (i.e. new blood vessel formation) in the yolk sac membrane at four days of development, subsequent to the application of test substance in a methyl cellulose pellet. The yolk sac membrane assay used is briefly described below.

Fertilized white Leghorn eggs were washed and incubated on an automatic egg turner in a 37.5° C. incubator with humidity at 50%. After two and a half days of incubation eggs were cracked by a sharp blow on the lower side and the contents delivered to prepared cultured chambers, similar to those developed by Dunn et al. (*Anat. Res.* 1991:33-43, 1981) consisting of a sling/cradle of "Clear Plastic Wrap" (Safeway Stores, Inc., Oakland, Calif.) supported in a 5 cm × 8 cm diameter section of a plastic drain pipe. The plastic film was secured by elastic bands and the chambers covered with loosely fitting plastic Petri dish lids (15×100 mm). The embryos were incubated at 37.5° C. for a further 24 hours before applying the test materials.

Samples were dissolved in sterile distilled water and diluted with sterile 1% methyl cellulose (USP 4000 centipose, Fisher Scientific Co., N.J.) or directly in sterile 1% methyl cellulose. Seven microliters of a solution in 1% methyl cellulose was placed on cross-sections of short sterile Teflon rods (2.4 mm diameter) and dried to discs in a sterile laminar flow of air at room temperature. Discs were placed approximately half way between the embryo and the boundary of the membrane. The chambers were covered and returned to a 37.5° C. humidified incubator after photographing the discs and proximal blood vessels under a dissecting microscope under 10-12X magnification. Observation and photography was repeated at 6 and 24 hours.

In this assay, a strong positive response consists of the development of a radial pattern of blood vessels around the test disc. Occasionally, a membrane opacity was noted at the center of the radial pattern. Weaker responses consist of the development of looping patterns of blood vessels near the disc. In all experiments, negative control pellets were applied to each egg and no responses were ever noted in these controls.

2. Angiogenesis Testing: The Rabbit Cornea Model

Angiogenesis or new capillary growth was assayed by implanting 20 ml pellets of test substance dispersed in Hydron into the cornea of rabbits as described by Banda et al. (*Proc. Natl. Acad. Sci.* 79:7773-7777, 1982) and was graded on a scale from 0 to 4+ as described by Hunt et al. (*Surg.* 96:48-54, 1984).

3. Wound Healing Assay: Wire Mesh Cylinder Model

This assay was carried out using so-called "Schilling/Hunt" chambers as described (White, B. M. et al. *Proc. Soc. Exp. Biol. Med.* 101:353-356, 1959; Schilling, J. A. et al. *Am. J. Surg.* 117:330-337, 1969). Cylinders (made in the inventor's laboratory) were implanted in rats as described by Goodson et al. (*J. Surg. Res.* 21:125-129, 1976). Beginning on day eight, each of the cylinders was injected with either phosphate buffered saline or a test substance. Injections were continued on a daily basis for 14 days prior to removal. After removal, the tissue in the chamber was analyzed for total DNA (Burton, K. *Biochem. J.* 62:315-323, 1956), total protein (Research Bulletin No. 20, Technicon Corporation, Ardsley, N.Y.) and total hydroxyproline (Jackson et al. *Meth. Biochem. Anal.* 15:25-77, 1967), the latter as a measure of collagen content. Other specimens of the tissue in the chamber were fixed and prepared for histological examination.

Samples obtained from the different fractionization procedures described above were screened for biological activity initially using the chick embryo angiogenesis assay. This procedure, which is relatively rapid, not only indicated the fractions in which major biological activity may reside, but also provided dose/response information for use in the next level of biological testing. Fractions of interest were subsequently tested in the rabbit eye angiogenesis model. These results were used in turn as a guide as to which fraction should be tested in the wound healing model using subcutaneously implanted wire mesh cylinders. The results are shown in Tables 2 and 3 below.

TABLE 2

| Fraction Gel Filtration | Bioassay of LYCD Fractions | | | | |
|---|---|---|---|---|---|
| | Yolk Sac Membrane Assay | | | Rabbit Cornea Assay | |
| | Amt Applied (micrograms) | Result | N | Amt Applied (micrograms) | Result** |
| Peptide Fraction | | | | | |
| FIG. 1 Fraction A | 1000 | + | 5/5 | | |
| | 500 | + | 5/5 | 25.2 | 4+4+ |
| | 250 | + | 4/5 | | |
| | 125 | + | 4/5 | | |
| | 64 | − | 12/12 | | |
| | 32 | − | 12/12 | | |
| Subfractions of peptide fraction | N.T.* | | | | |
| FIG. 2 Fraction A | | | | 2.4 | 3+3+ |
| FIG. 2 Fraction B | | | | 7.7 | 3+2+ |
| FIG. 2 Fraction C | | | | 13.0 | 3+2+ |
| FIG. 2 Fraction D | | | | 7.0 | 4+4+ |
| Mixed Amino Acids & Carbohydrate | 430 | − | 12/12 | 756 | 1+0 |
| | 43 | − | 12/12 | | |
| FIG. 1 Fraction B Ion Exchange Chromatography | | | | | |
| Mixed Peptides & Amino Acids | 1680 | + | 5/6 | 1680 | 1+1+ |
| | 340 | + | 6/6 | | |
| FIG. 5 Fraction B | 170 | + | 3/6 | 168 | 1+1+ |
| Amino Acid Fraction*** | 1000 | − | 12/12 | N.T.* | |
| | 550 | − | 12/12 | | |

TABLE 2-continued

|  | Bioassay of LYCD Fractions | | | | |
|---|---|---|---|---|---|
|  | Yolk Sac Membrane Assay | | | Rabbit Cornea Assay | |
| Fraction Gel Filtration | Amt Applied (micrograms) | Result | N | Amt Applied (micrograms) | Result** |
| Carbohydrate Fraction | 3500 | — | 12/12 | N.T.* | |
| FIG. 5 Fraction A | 1750 | — | 12/12 | | |

*N.T. = not tested.
 Number of positive or negative results compared to total number of disks applied.
**Results scored for each of two eyes.
***Isolated from Fraction B FIG. 5 by gel filtrationon Sephadex G-25.

In Table 2 above, it can be seen that the peptide fraction (A from FIG. 1) elicited a positive response when applied to chick embryo yolk sac membranes. A radial pattern of blood vessels could be detected when as little as 125 micrograms was applied. Samples of the mixed peptide fraction isolated by the ion exchange procedure (Fraction B from FIG. 5) also elicited a positive response in the chick embryo assay at dose levels as low as 170 micrograms applied but the amino acid fraction isolated from this by gel filtration was negative. The carbohydrate or trehalose fraction was negative even at a dose level as high 3.5 mg.

Results of the yolk sac membrane assay, therefore, indicated that the highest activity resided in the higher molecular weight peptides which can be isolated either directly by gel filtration or by an ion exchange procedure followed by gel filtration. The fraction containing free amino acids was negative.

Results obtained from the rabbit eye angiogenesis model bore out these results. Thus, the peptide fraction (Fraction A, FIG. 1) demonstrated a 4+ response in two eyes at a concentration of 25.2 micrograms applied. Individual subfractions A-D of FIG. 2 gave positive responses when as little as 2.4 micrograms was applied (Table 2), fractions A and D being the most active fractions. The mixed peptide and amino acid fraction gave marginally positive results at higher dose levels (168 micrograms) presumably due to the presence of small amounts of high molecular weight peptides in this fraction.

Histological sections of the corneas implanted with Hydron showed a non-specific, acute inflammatory reaction at two days post-implantation. At eight days there was a light sprinkling of mononucleated cells in the vicinity of the implant. These cells were not concentrated around the implant, and although easily seen were remarkably sparse.

Based upon the above angiogenesis screening procedures, the most active fraction (Fraction A, FIG. 1) which was a mixture of peptides with molecular weights ranging between about 6,000 daltons and about 17,000 daltons was injected into subcutaneously implanted wire mesh cylinders in rats at dose levels of 200 micrograms/day and 20 micrograms/day for 14 days. The results are set forth in Table 3 below.

TABLE 3

| | Stimulation of Wound Healing in Wire Mesh Cylinders | | | | | |
|---|---|---|---|---|---|---|
| | Daily Injection of | | | Daily Injection of | | |
| | PBS* | LYCD 5 mg | LYCD 0.5 mg | PBS | Peptide Fraction 200 micrograms | Peptide Fraction 20 micrograms |
| DNA (mg/cylinder) | 348.7 ± 22.6 | 1077.0 ± 74.5 | 751.9 ± 93.4 | 391.9 ± 34.5 | 1005.9 | 635.9 ± 23.8 |
| Hydroxyproline (mg/cylinder) | 625.3 ± 37.1 | 975.3 ± 44.6 | 911.2 ± 67.2 | 657.6 ± 34.3 | 1116.8 ± 49.8 | 807.2 ± 51.3 |
| Protein (mg/cylinder) | 39.7 ± 4.7 | 110.3 ± 9.0 | 78.3 ± 11.2 | 36.6 ± 5.7 | 92.8 ± 4.8 | 69.5 ± 6.9 |

Results expressed as X ± 1 SEM (n = 6 or at a minimum 5 for each condition).
All experimental values are significantly different from controls by Students t-test.
*Phosphate buffered isotonic saline solution.

The results in Table 3 indicated that the injection of whole LYCD at two different concentrations provoked a very large response in all three of the measured parameters (DNA, protein and hydroxyproline synthesis). These are well accepted as markers of a wound healing response. These results were duplicated by the injection of the peptide fraction but at a 25-fold lower concentration. The parameters measured, i.e. total DNA, protein and hydroxyproline synthesis, indicated a large increase in each of these parameters. Biological examination of the tissue from the cylinder showed minimal inflammatory response and appeared very similar to the response obtained by the injection well-known growth factors such as epidermal growth factor (EGF) although the latter was active at lower concentrations (data not shown).

What is claimed is:

1. A purified isolated mixture of angiogenic polypeptides having molecular weights ranging between about 6,000 daltons and about 17,000 daltons as determined by SDS-PAGE, said polypeptides isolated from live yeast cell derivative.

2. The polypeptides of claim 1, wherein said live yeast cell derivative is obtained from *Saccharomyces cervisiae*.

3. A pharmaceutical formulation for treating wounds or burns in mammals comprising an effective amount for treating wounds or burns of a purified isolated mixture of angiogenic polypeptides having molecular weights ranging between about 6,000 daltons and about 17,000 daltons as determined by SDS-PAGE, said factor isolated from a live yeast cell derivative, and a pharmaceutically acceptable carrier.

4. The pharmaceutical formulation of claim 3, wherein said live yeast cell derivative is obtained from *Saccharomyces cervisiae*.

5. A method for treating a mammal suffering from wounds or burns comprising administering to a mammal in need of the treatment an effective amount of the purified isolated mixture of angiogenic polypeptides having molecular weights ranging between about 6,000 daltons and about 17,000 daltons as determined by SDS-PAGE, said polypeptides isolated from a live yeast cell derivative.

6. A purified isolated mixture of angiogenic polypeptides isolated from a live yeast cell derivative comprising polypeptide fractions A–D, said polypeptide fractions having the amino acid compositions:

|  | A | B | C | D |
|---|---|---|---|---|
| ASP | 115 | 132 | 138 | 64 |
| THR | 102 | 67 | 41 | 21 |
| SER | 117 | 89 | 76 | 32 |
| GLU | 135 | 156 | 157 | 249 |
| PRO | 51 | 43 | 50 | 22 |
| GLY | 110 | 118 | 128 | 304 |
| ALA | 137 | 129 | 110 | 47 |
| ½ CYS | 4 | 3 | 7 | 117 |
| VAL | 49 | 50 | 50 | 25 |
| MET | 4 | 10 | 11 | 10 |
| ILE | 25 | 19 | 20 | 13 |
| LEU | 31 | 34 | 41 | 30 |
| TYR | 2 | 1 | 1 | 2 |
| PHE | 19 | 19 | 18 | 9 |
| HIS | 11 | 12 | 16 | 8 |
| LYS | 74 | 100 | 115 | 36 |
| ARG | 15 | 19 | 20 | 11 | said compositions based upon amino acid residues per 1000 residues.

* * * * *